(12) United States Patent
Buttler et al.

(10) Patent No.: US 9,023,057 B2
(45) Date of Patent: May 5, 2015

(54) IMPACTING DEVICE AND METHOD

(71) Applicant: DePuy Synthes Products, LLC, Raynham, MA (US)

(72) Inventors: Markus Buttler, Oensingen (CH); Patrick Streff, Weil am Rhein (DE)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/473,078

(22) Filed: Aug. 29, 2014

(65) Prior Publication Data

US 2014/0371754 A1 Dec. 18, 2014

Related U.S. Application Data

(63) Continuation of application No. 13/298,769, filed on Nov. 17, 2011, now Pat. No. 8,845,651, which is a continuation of application No. 11/447,385, filed on Jun. 5, 2006, now Pat. No. 8,080,015, which is a continuation of application No. PCT/IB2004/002601, filed on Aug. 11, 2004.

(51) Int. Cl.
| | |
|---|---|
| *B25D 9/00* | (2006.01) |
| *B25D 11/00* | (2006.01) |
| *B25D 13/00* | (2006.01) |
| *E21B 1/00* | (2006.01) |
| *F16B 17/00* | (2006.01) |
| *B25D 1/00* | (2006.01) |
| *B25D 1/16* | (2006.01) |
| *A61B 17/58* | (2006.01) |
| *A61B 17/60* | (2006.01) |
| *A61F 2/00* | (2006.01) |
| *A61B 17/92* | (2006.01) |
| *B25D 1/04* | (2006.01) |
| *B25D 1/14* | (2006.01) |
| *A61B 17/16* | (2006.01) |
| *A61B 17/88* | (2006.01) |
| *A61B 17/90* | (2006.01) |

(52) U.S. Cl.
CPC .............. *A61B 17/92* (2013.01); *Y10T 403/70* (2013.01); *A61B 17/1697* (2013.01); *A61B 17/8861* (2013.01); *A61B 17/921* (2013.01); *A61B 2017/922* (2013.01); *B25D 1/04* (2013.01); *B25D 1/14* (2013.01); *A61B 2017/90* (2013.01)

(58) Field of Classification Search
USPC ............ 606/99, 100; 81/27; 403/345; 173/90
See application file for complete search history.

(56) References Cited

U.S. PATENT DOCUMENTS

| 1,055,058 | A | * | 3/1913 | Leighton | 223/102 |
|---|---|---|---|---|---|
| 5,694,672 | A | * | 12/1997 | Perin | 29/426.5 |
| 8,080,015 | B2 | * | 12/2011 | Buttler et al. | 606/100 |
| 8,845,651 | B2 | * | 9/2014 | Buttler et al. | 606/99 |
| 2005/0240197 | A1 | * | 10/2005 | Kmiec, Jr. | 606/100 |

* cited by examiner

*Primary Examiner* — David Bates
(74) *Attorney, Agent, or Firm* — Fay Kaplun & Marcin, LLP

(57) ABSTRACT

An impacting device for inserting, positioning and/or removing an implant and/or performing other impacting applications. The impacting device may have a head having at least one recess. The recess may have a insertion channel and a locking chamber. In one embodiment, the insertion channel and the locking chamber may be connected by an axial channel. The recess may pass through a lateral surface of the head so that the base surface may remain cohesive or unobstructed. A guide means, such as a guide rod, may be positioned though the recess so that the head may be moveable on the guide means and not disengage the guide means. A shaft having a handle may be attached to the head to assist a surgeon in moving the head on the guide means.

20 Claims, 8 Drawing Sheets

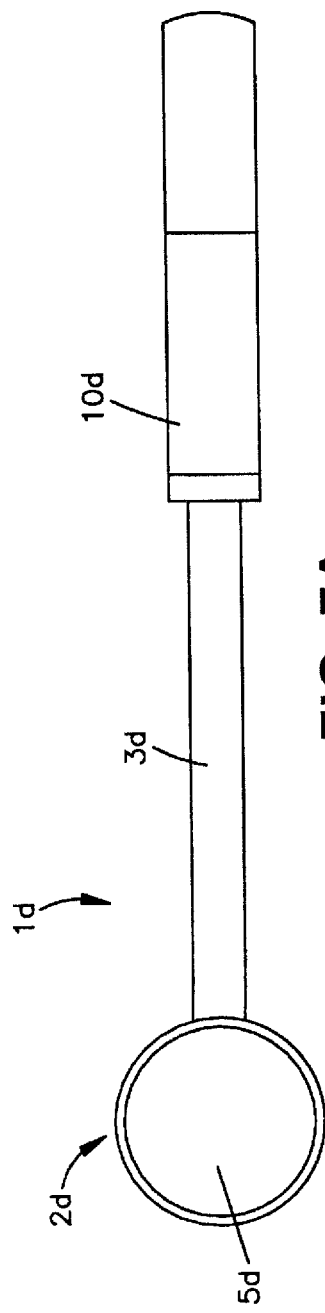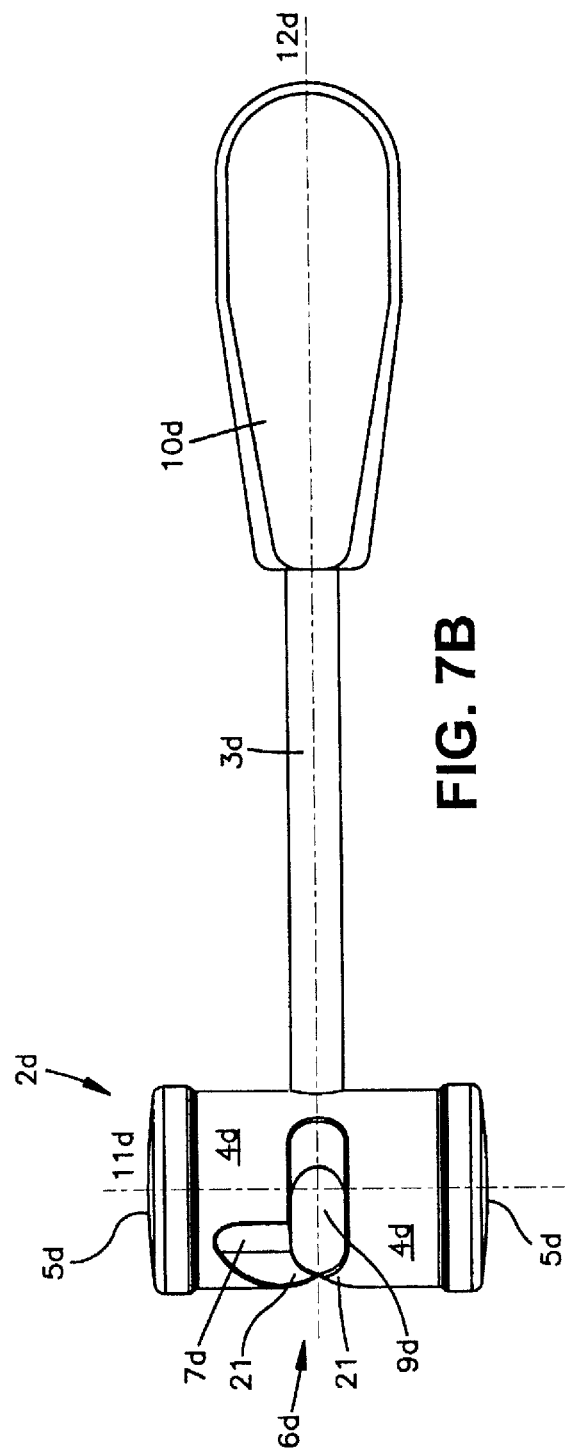

IMPACTING DEVICE AND METHOD

CROSS REFERENCE TO RELATED APPLICATION

The present application is a Continuation Application of pending U.S. patent application Ser. No. 13/298,769 filed on Nov. 17, 2011, now U.S. Pat. No. 8,845,651; which is a Continuation Application of U.S. patent application Ser. No. 11/447,385 filed on Jun. 5, 2006, now U.S. Patent No. 8,080,015; which is continuation of PCT Application No. PCT/IB2004/002601 filed on Aug. 11, 2004. The disclosures of the above applications/patents are incorporated herein by reference.

FIELD OF THE INVENTION

A device and method for impacting surgical devices and, in particular, an impacting device for inserting, positioning and/or removing an implant and/or performing other impacting applications in surgery.

BACKGROUND OF THE INVENTION

In general, surgical mallets are known which are guided on devices for the insertion and/or extraction of implants, in particular intramedullary nails. U.S. Pat. No. 5,476,467 and WO 80/00534 disclose a mallet having a cylindrical shape and a centered bore which follows the longitudinal axis and by means of which the mallet slides over the insertion or extraction device. Guidance of these mallets may be difficult since the surgeon can only exert force on the mallet by gripping the cylinder on its lateral surface by hand. Moreover, these mallets can be used only with a particular insertion device.

Improved surgical mallets, such as those disclosed in U.S. Pat. No. 5,913,860 and in DE 19860569, disclose mallets which have a cylindrical mallet head and a mallet shaft for facilitating guidance of the surgical mallet. The surgical mallet of U.S. Pat. No. 5,913,860 not only has a cylindrical bore but also has a recess so that the surgical mallet can be introduced after assembly of the insertion device. Thus, this surgical mallet is universally applicable and, consequently, can be used as a mallet for directly driving, for example, nails into tissue. However, the guidance of the mallet on the insertion device may be complicated. Due to the slotted design, the mallet head may not be securely held on the implantation device (e.g., a guide rod) and, upon moving the mallet, the mallet may slip off the guide rod. As a result, the precision of a procedure may be impaired and the danger of injury may increase for the surgeon and others.

Furthermore, in a mallet embodiment having a slotted design, the slot intersects the base or impact surface of the cylindrical mallet head (i.e., the surface which is used for striking/impacting). Use of the mallet is complicated since it is necessary to ensure that the nail head, the nail end or other instruments which are used for insertion are struck with the intact surface and not in the area where a slot intersects the base surface. Therefore, the lateral or side surface of mallets designed in this manner (i.e., with a slot intersecting the base) are usually used as the impacting surface to impact an instrument. However, when hammering with the side surface of the mallet, the mallet head tends to be springy upon impact.

U.S. Pat. No. 6,592,590 discloses a surgical mallet which has a guide channel for a guide rod. The guide channel is designed so that the mallet head is prevented from being removed from the guide rod in the lateral direction. The impact surface of the mallet head is interrupted, so that the mallet can be reliably used only in combination with a guide rod. The mallet head tends to slip downwards from the guide rod on slight canting of the head. This may happen quickly since movement of the mallet on the guide rod is contradictory to natural human movement when impacting an object vertically. It is more advantageous to move the mallet in a gentle arc. However, it is the arc movement which leads to the guide rod slipping out of the slot of the mallet head.

It is desirable to have an impacting device, which provides the device for insertion and/or extraction of the implant (e.g., a guide rod), with guidance. Moreover it is desirable to have a impacting device, which may be attached to a guide rod after attaching the guide rod to an implant, is reliable for use in striking an implant and can be used universally with different types of guide rods and/or implants.

SUMMARY OF THE INVENTION

The impacting device may have a head having a longitudinal axis, a lateral surface and at least one base surface; and a recess positioned in the head which may have a first channel and a second channel. A shaft may be operably associated with the head and a handle may be operably associated with the shaft. The handle may have at least one flat side.

The first and second channels may be separated a distance from each other and operably connected to each other. The first and second channels may intersect the lateral surface. The first channel may be an insertion channel for receiving a guide means and the second channel may be a locking chamber for attaching the guide means to the head. The locking chamber may be sized and configured so that the head may be rotatable about the longitudinal axis on the guide means. At least one spherical pressure pin may be positioned in the locking chamber of the head to keep the guide means in the locking chamber.

Moreover, the head may have a third channel which may connect the first and second channels. The third channel may be an axial channel extending parallel to the longitudinal axis. The first channel may be in a first plane, the second channel may be in a second plane and the third channel may be in a third plane. The first and second planes may be parallel to each other and the third plane may be perpendicular to the first and second planes. The first and second channels may have an angle therebetween, wherein the angle may be between about 20° and about 150°.

In an alternative embodiment, the impacting device may have a head having a longitudinal axis, a lateral surface and at least one base surface; and a recess positioned in the head which may have a first channel and a second channel. The first and second channels may be operably connected to each other and may be at an angle with respect to each other. The first channel may be an insertion channel and the second channel may be a locking chamber for receiving a guide means. The locking chamber may have at least one protrusion for holding the guide means in the locking chamber. The locking chamber may be sized and configured so that the head may be rotatable on the guide means about the longitudinal axis. The locking chamber may have a first sloping surface and a second sloping surface. The first and second sloping surfaces may form a V-shape.

A method of inserting or removing a device/implant from tissue may comprise providing an impacting device comprising a head having a longitudinal axis, a lateral surface and at least one base surface; and a recess positioned in the head having a first channel, a second channel and a third channel connecting the first and second channel. The method may further comprise inserting the guide means into the first channel in a direction perpendicular to the longitudinal axis; moving the guide means through the third channel along the longitudinal axis; inserting the guide means into the second channel; and rotating the guide means within the second channel so that the head may be moveable along the guide means. The impacting device may designed to allow a surgeon to move his/her hand and/or a handle of the device in an arc-like manner as the head moves along the guide means.

Alternatively, the method of inserting or removing a device from tissue may include providing an impacting device comprising a head having a longitudinal axis, a lateral surface and at least one base surface; and a recess positioned in the head which may have a first channel and a second channel, the first and second channels may be operably connected to each other, wherein the first and second channels may be at an angle with respect to each other. The method may further include inserting a guide into the first channel, rotating the guide means to position the guide means from the first channel into the second channel, and rotating the head about the longitudinal axis as the head is moved along the guide means.

The design of the impacting device may allow the impacting device to be used as a normal mallet for striking. Consequently, a surgeon may use the impacting device with a guide means to insert/extract an implant as well as freely striking a tool or tissue (i.e., without guidance).

Owing to the design of the recess in the head of the impacting device, various improvements may achieved over previous devices. Although the head of the impacting device may be inserted after assembly of the device for insertion and/or extraction, a type of locking of the head by means of the device may be achieved. By providing separate regions, such as insertion channel, axial channel and locking chamber, the insertion of the guide rod may so complex that it may be possible to remove the head from the device only through a bayonet connection-like movement in the opposite direction of insertion. The head remains fixed by the device during striking because the movement necessary to remove the head from the recess is not carried out during striking. Since injuries and damage to implants and instruments often occur as a result of imprecise impacts, the reliable guidance of the head on the guide means may permit precise impacts, which may have a noticeable positive effect both when driving in and when driving out implants. Furthermore, as a result of the design of the recess in the head, the full impact force may be maintained.

In one embodiment, the recess may be provided only in the lateral surface so that the base surfaces may remain intact. Consequently, the entire base surfaces of the impacting device may be maintained as impact surfaces. However, even if the recess is positioned so that the recess was positioned through the base surfaces, the impact force on the lateral surfaces may be substantially maintained because springiness during striking may be substantially prevented. The reduction/elimination of springiness may be due to the bayonet connection-like arrangement of insertion channel, axial channel and locking chamber of the recess. Furthermore, if the center of gravity of the head is located in the extrapolated axis of the shaft or in the axis of a guide rod, the danger of canting during sliding on the guide rod may also be minimized.

BRIEF DESCRIPTION OF THE DRAWINGS

The impacting device can be better understood by reference to the following drawings, wherein like reference numerals represent like elements. The drawings are merely exemplary to illustrate certain features that may be used singularly or in combination with other features and the impacting device should not be limited to the embodiments shown.

FIGS. 7A and 7B are different views of an alternative exemplary embodiment of an impacting device;

DETAILED DESCRIPTION

The impacting device may be used for insertion and/or extraction of implants, for example, intramedullary rods/nails and Kirschner wires. The impacting device may also be used for impacting other instrumentation positioned in the body. The impacting device may have a head and at least one recess for receiving a guide means such as a guide rod. In some embodiment, the impacting device may have a shaft for moving the head. It should, however, be understood that those of ordinary skill in the art will recognize many modifications and substitutions which may be made to various elements of the impacting device.

Figure 1:
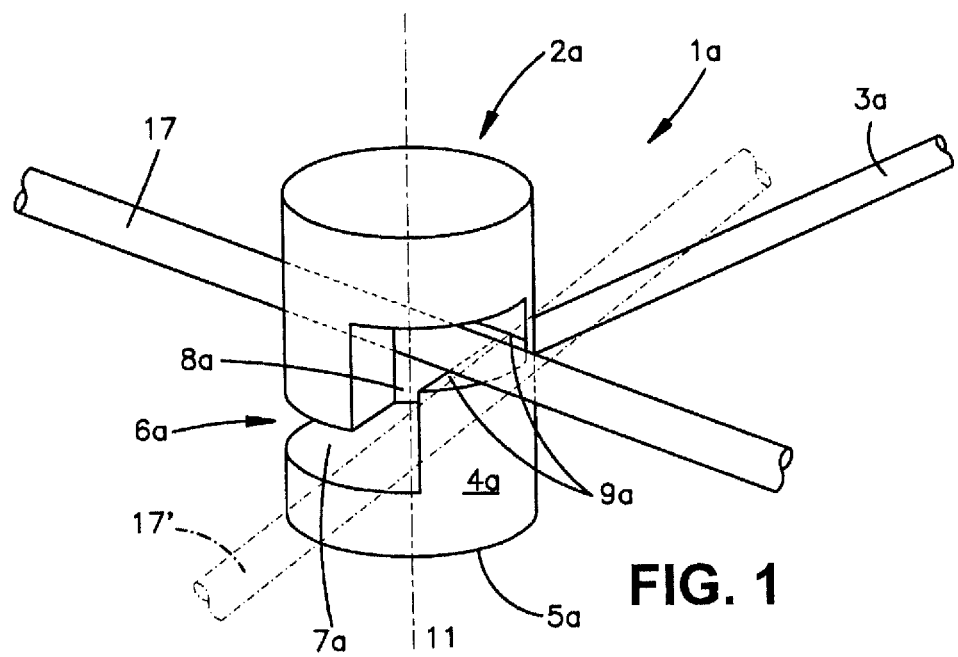
FIG. 1 is a perspective view of an exemplary embodiment of an impacting device illustrating various orientations of a guide means positioned through the device.

FIG. 1 illustrates an impacting device 1a attached to a guide means such as guide rod 17, an extraction rod or a sliding rod. The impacting device 1a may have a head 2a and a shaft 3a. The head may be an shape. In a preferred embodiment, the head 2a may be generally cylindrical in shape.

Figure 3B:
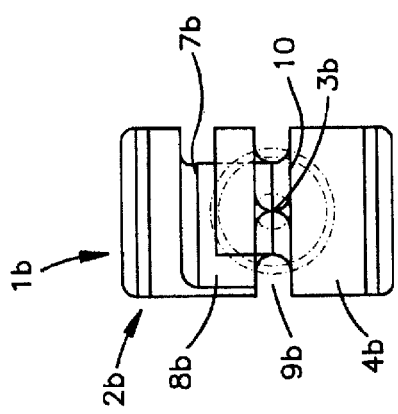
FIGS. 3A, 3B and 3C are different views of an exemplary embodiment of the impacting device of FIG. 1.
Figure 3A:
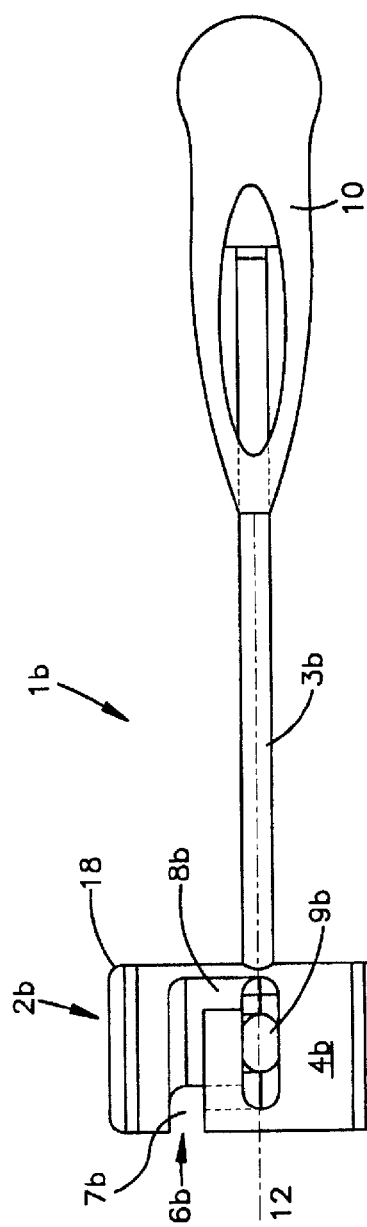
Figure 3C:
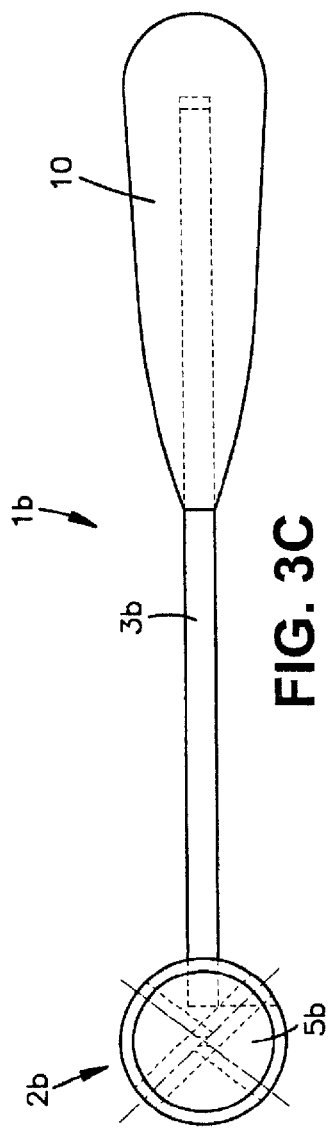

The head 2a may have a lateral surface 4a, base surface(s) 5a and at least one recess 6a. The recess 6a may be slot-like. The recess 6a may have guide regions such as an insertion channel 7a into which a guide means may be initially inserted into the head 2a and a locking chamber 9a into which the guide means may be received so that the head 2a may be guided for impacting/striking. The locking chamber 9a may be oriented radially and/or may be an elongated hole. In one embodiment, the insertion channel 7a and locking chamber 9a may not directly intersect (e.g., the planes of the insertion channel 7a and locking chamber 9a may be approximately parallel to each other). In such an embodiment, the insertion channel 7a and locking chamber 9a may be connected to each other by another guide region such as axial channel 8a. As shown in FIGS. 3A and 3B, the plane of the insertion channel 7a and/or the locking chamber 9a may be perpendicular to the plane of the axial channel 8a.

The dimension of the recess 6a may depend on the device to be inserted therein. For example, the dimension of the recess 6a may be adapted to receive the guide rod 17. The insertion channel 7a and the locking chamber 9a may be positioned at an angle $\alpha$ (FIG. 4D) relative to each other. The angle $\alpha$ may be, for example, between about 10° and about 160°, more preferably, between about 20° and about 150°, even more preferably, between about 20° and about 70° and, most preferably, between about 30° and about 40°. In another embodiment, a preferred angle between the insertion channel 7a and the locking chamber 9a may be about 80°. The angle may be chosen so that, once inserted into the locking chamber 9a, the guide rod 17 does not move out of the locking chamber 9a and/or axial channel 8a during the sliding/impacting operation. Moreover, the insertion chamber 7a may be arranged at an angle to the axial channel 8a. For example, the insertion channel 7a may be arranged at an angle to the axial channel 8a of between about 20° and about 160° and, more preferably, between about 30° and about 150°. In one embodiment, a preferred angle between the insertion channel 7a and the axial channel 8a may be about 80°. Furthermore, the insertion channel 7a may be arranged at an angle to the longitudinal axis 11 of the head 2a of between about 20° and about 70° and, more preferably, between about 40° and about 50°.

The axial channel 8a may be positioned parallel to the longitudinal axis 11. In one embodiment, the axial channel 8a may be in a plane which may extend along the longitudinal axis 11. In an alternative embodiment, the recess 6a may be formed in a base surface 5a as well as the lateral surface 4a. In such an embodiment, the axial channel 8a may be approximately perpendicular to the longitudinal axis 11 of the head 2a.

The guide regions (i.e., insertion channel 7a, axial channel 8a and locking chamber 9a) may occupy a space inside the head 2a which may not coincide with another space or region. The recess 6a may be designed so that the guide means or device for insertion and/or extraction may be inserted with a bayonet-like connection. Guide means or device for insertion and/or extraction of implants may pass through the entire extent of one region before reaching the next, adjacent region. For example, the guide means may necessarily pass entirely through the insertion channel 7a before entering the axial channel 8a and the guide means may necessarily pass entirely through the axial channel 8a before entering the locking chamber 9a. In this way, the guide means may experience improved guidance. The. recess 6a may be designed so that, in order to insert a guide means such as guide rod 17 into the head 2a, at least one predominantly horizontal, at least one predominantly vertical insertion movement and a rotational movement may be required. Such a technique is in contrast to existing slotted mallets which may require an individual horizontal or vertical movement, or a horizontal and a tilting movement.

The guide means is not only guided in the recess 6a, but may be locked in the locking chamber 9a so that the guide means may not detach from the head 2a during impacting or the insertion/extraction process. Moreover, the locking chamber 9a may have additional locking elements such as, for example, spherical pressure pins for holding a guide means in the locking chamber 9a. The arrangement of the components/guide regions of the recess 6a may prevent the guide means from becoming disengage from the head 2a during hammering. Even if the impacting device 1a were to be driven in a slightly canted manner, the head 2a does not disengage (slip off) the guide means or guide rod 17. Moreover, the striking direction may be more comfortable for the surgeon since a certain play may remain in the locking chamber 9a. In particular, it may be possible for a surgeon to execute a gentle arc with his/her hand and/or a handle of the device during striking while, at the same time, reliably guiding the guide rod 17. For example, the head 2a may rotate about its longitudinal axis 11 during the striking movement. It should be noted that the impact direction may be substantially perpendicular to the longitudinal axis 11 of the head 2a.

Figure 2A:
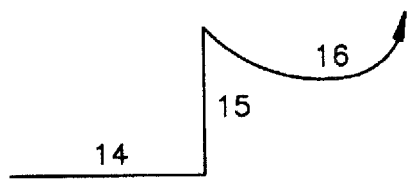
FIGS. 2A and 2B are schematic diagrams of the movement of a guide means through a recess of the impacting device.
Figure 2B:
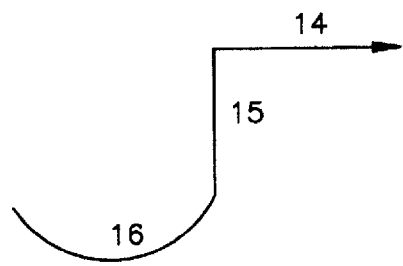

A guide means such as guide rod 17 may be inserted into the recess 6a of the impacting device 1a. The guide rod 17 may be moved from a first position immediately upon insertion into the recess 6a (shown by rod 17' in dashed lines) to a second position (shown by rod 17) (i.e., the position in which the impacting device 1a may be guided along the guide rod 17). The manner of inserting a guide means, such as guide rod 17, into the recess 6a is shown in FIGS. 2A and 2B. In particular, FIGS. 2A and 2B illustrate the movement of a guide rod 17 into the recess 6a. All designations of the direction of movement in the description of FIGS. 2A and 2B relate to the longitudinal axis 11 of the head 2a. Upon insertion of the guide rod 17 into the insertion channel 7a, the guide rod 17 may be moved radially towards the longitudinal axis 11—radial movement 14. Thereafter, the guide rod 17 may be guided (translated) along or parallel to the longitudinal axis 11 of the head 2a (i.e., the guide rod 17 may be moved axially)—axial movement 15. For example, the guide rod 17 may be moved down along the axis 11 or axial channel 8a. After reaching the plane of the locking chamber 9a, the guide rod 17 may be rotated—rotational movement 16—so that the rod 17 may be locked in the head 2a of the impacting device 1a. As shown in FIG. 1, the guide rod 17 may be rotated counterclockwise within the locking chamber 9a about the longitudinal axis 11. It should be noted that in other embodiments, the recess 6a may be configured so that the guide rod 17 may be rotated clockwise within the locking chamber 9a to fix the rod 17 within the head 2a.

In another configuration of the recess 6a, the rod 17 may be inserted into the insertion channel 7a and rotated—rotational movement 16—for example, about the longitudinal axis 11 or about a line parallel to the axis 11. The rotation may be clockwise or counterclockwise depending on the configuration of the recess 6a. Thereafter, axial movement 15 (e.g., along the axis 11 or along a line parallel to the axis 11) may be executed, followed by radial movement 14 (e.g., toward the axis 11). In another embodiment, the axial channel 8a may be sized and configured so that a guide means may rotate and move axially within the axial channel 8a. In such an embodiment, the guide means may be moved radially within the insertion channel 7a and the locking chamber 9a. Those skilled in the art will appreciate that the recess 6a may be configured in any other way so long as the recess 6a has a plurality of separate regions by which a guide means may be locked and guided after insertion into the recess 6a.

Since the recess 6a is provided in the lateral surface 4a of the head 2a, the base surfaces 5a may remain intact, uninterrupted, solid or cohesive (i.e., there are no interruptions or slots in the surfaces 5a). Consequently, in an embodiment where no guide means is used the base surfaces 5a may provide a regular impact surface.

The shaft 3a may be attached to the head 2a to provide an operator with a surface to grip so that the operator may move the head 2a along a guide means and/or impact the head 2a with another device or tissue. The shaft 3a may be integral with or attachable to the head 2a. Moreover, the shaft 3a may be fixed and/or rotatable relative to the head 2a. Those skilled in the art will appreciate that a head 2a may be formed without a shaft 3a.

The shaft 3a may be any shape or size so long as the surgeon may grasp the shaft 3a and use the shaft 3a to move the head 2a. For example, the shaft may be cylindrical or polygonal. In some embodiment, the shaft 3a and/or a handle (not shown) attached to the shaft 3a may be ergonomically designed so that the shaft 3a and/or handle may fit comfortable into an operator's hands. For example, the shaft 2a may have an anatomically shaped handle with, for example, two approximately parallel gripping surfaces (not shown) which are each in a plane normal to the base surfaces 5*b*.

An alternative impacting device 1*b* is illustrated in FIGS. 3A-3C and 4A-4D. Similar to the impacting device 1*a* of FIG. 1, the impacting device 1*b* may have a head 2*b* and a shaft 3*b* which may be welded to each other. Alternatively, the shaft 3*b* may be connected to the head 2*b* at a pivot so that the head 2*b* and shaft 3*b* may rotate relative to each other. The head 2*b* and the shaft 3*b* made be made of metal which may be suitable for medical purposes such as, for example, stainless steel, titanium or chromium-nickel (e.g., 5CrNiCuNb16-4).

A handle 10 may be provided on the shaft 3*b* and may be connected to the shaft 3 by, for example, pins. The handle 10 may have at least one flattened side so as to provide an enhanced gripping surface for a surgeon and to ensure that the impacting device 1*b* rests in the correct position in the hand. The handle 10 may be formed from a material which may have a good grip but which may be readily sterilizable. For example, the handle 10 may be made of plastic, ceramic, wood, metal or a composite material (i.e., two or more materials).

FIGS. 4A-4D illustrate different views of the head 2*b*. The head 2*b* may have a substantially cylindrical shape and rounded edges 18 may be provided between the lateral surface 4*b* and the base surfaces 5*b*. Such a configuration may result in a difference in design from FIG. 1. Those skilled in the art will appreciate that the head 2*b* may also be non-cylindrical in shape. The lateral surface 4*b* may be barrel shaped or may comprise cylindrical or flat impact surfaces and the base surfaces 5*b* may be barrel-shaped.

Figure 4A:
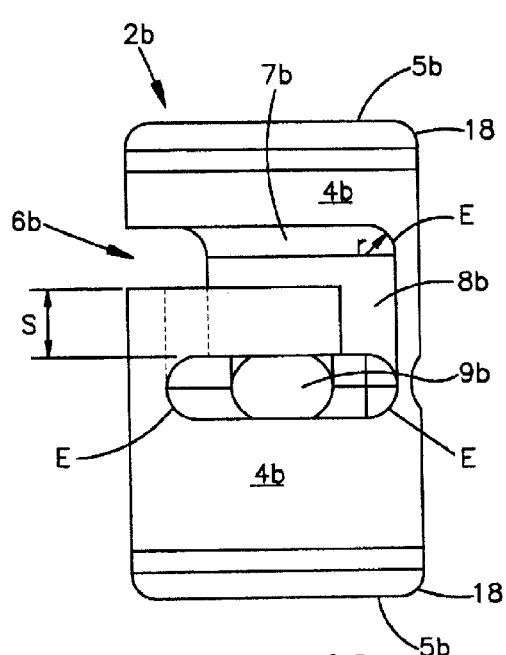
FIGS. 4A, 4B, 4C and 4D are different views of an exemplary embodiment of the head of the impacting device of FIGS. 3A-3C.
Figure 4B:
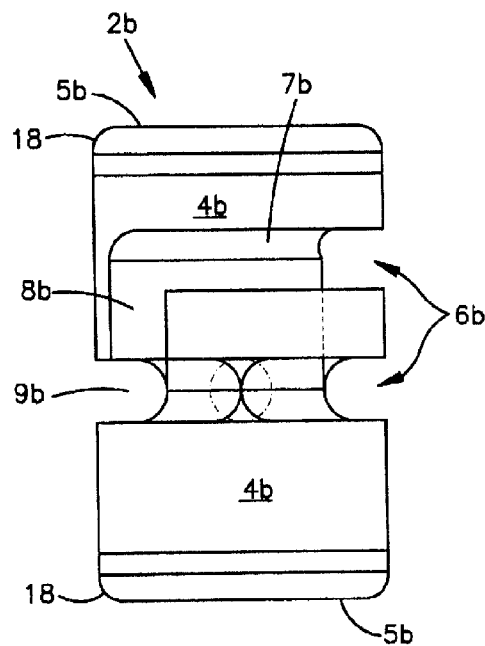
Figure 4C:
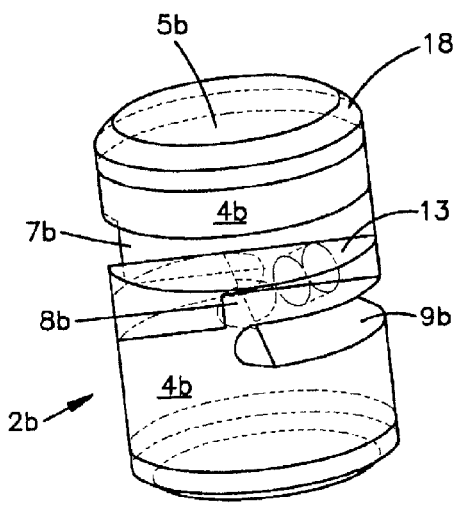
Figure 4D:
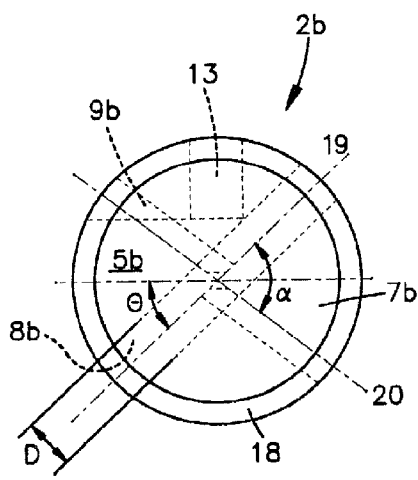

The head 2*b* may have at least one recess 6*b* for receiving a guide means (e.g., a guide rod 17, extraction rod or sliding rod) for insertion and/or extractions of implants. The recess 6*b* may also include an insertion channel 7*b*, a locking chamber 9*b* and an axial channel 8*b* positioned between the insertion channel 7*b* and the locking chamber 9*b*. The insertion channel 7*b* and the locking chamber 9*b* may be positioned at an angle relative to one another. FIG. 4D shows the longitudinal axis 19 of a guide rod (not shown) in the insertion channel 7*b* and the longitudinal axis 20 of the guide rod (not shown) in the locking chamber 9*b*.

The shaft 3*b* may be arranged off-center to the head 2*b* so that the center of gravity of the head 2*b* may pass through an extrapolation of the shaft axis 12. Because of the recess 6*b*, one region of the head 2*b* may be lighter than the other region. For example, as shown in FIGS. 4A and 4B, the recess 6*b* may be in the upper region of the head 2*b* and, therefore, may be lighter (i.e., weigh less) than the lower region, which may be substantially solid. Consequently, the attachment 13 of the shaft 3*b* may be displaced in the direction towards the lower region of the head 2*b* as shown in FIGS. 4B and 4C. The locking chamber 9*b* and attachment 13 of the shaft 3 may be approximately in the same plane. In this way, guidance of the device to the impacting surface by a guide means may be facilitated. Moreover, since the recess 6*b* and the insertion channel 7*b* may be positioned off-center in the head 2*b*, there may be less risk of vibration when the upper base surfaces 5*b* is used for striking.

Figure 5:
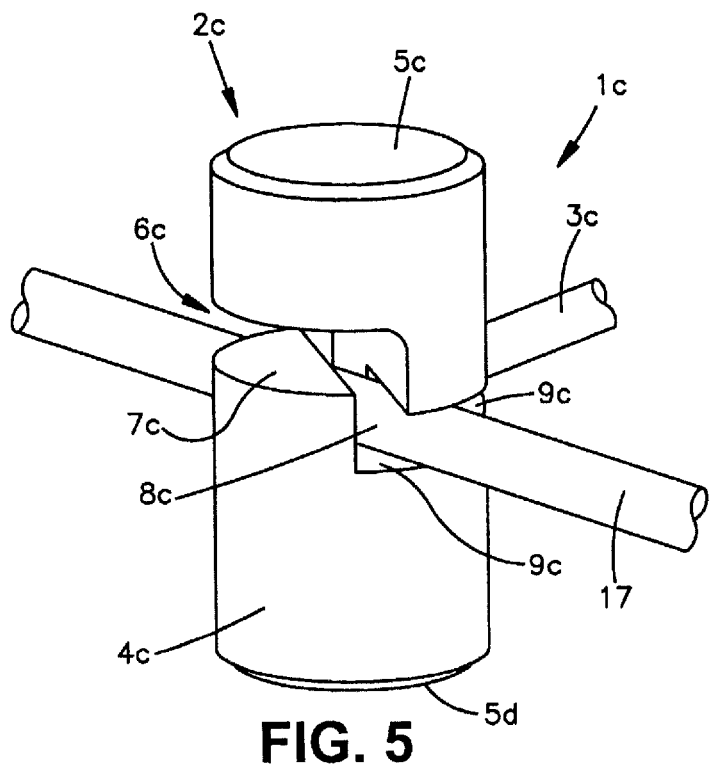
FIG. 5 is a perspective view of the impacting device of FIG. 1 positioned on a guide means.
Figure 6:
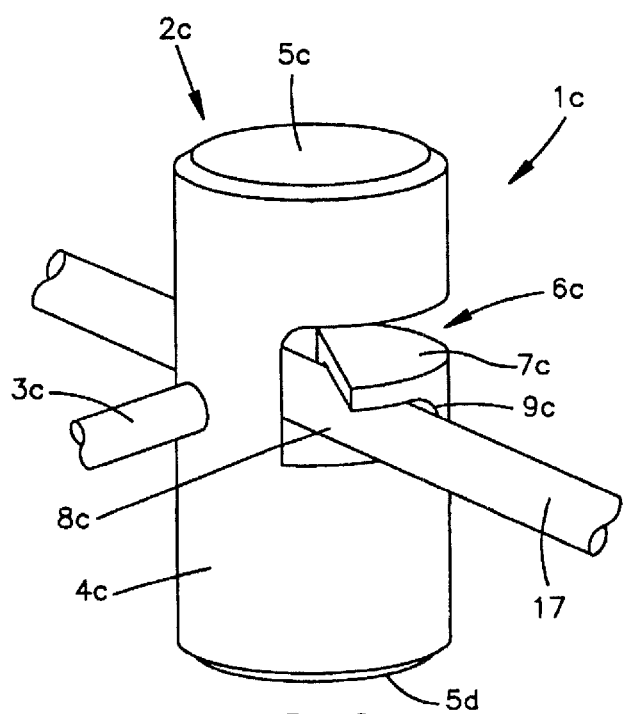
FIG. 6 is an alternative view of the impacting device of FIG. 5.

FIGS. 5 and 6 illustrate the impacting device 1*c* with a head 2*c*, a shaft 3*c* and a guide rod 17 positioned within the locking chamber 9*c*. With the guide rod 17 in the locking chamber 9*c*, the head 2*c* of the impacting device 1*c* may be moved along the guide rod 17 to extract or insert an implant. The head 2*c* may have an insertion channel 7*c*, an axial channel 8*c* and a locking chamber 9*c*. Three regions may be formed in the head 2*c*—a middle region which may have the insertion channel 7*c*, the axial channel 8*c* and the locking chamber 9*c* as well as end regions on either side of the middle region. The end regions may have no passages therethrough (i.e., the end regions may be solid). In particular, since the recess 6*c* may be formed in the lateral surface 4*c*, the base surfaces 5*c* and 5*d* may be solid impact surfaces which may be free of passages.

The impacting device 1*a*, 1*b* and 1*c* may be used in a conventional manner to directly or indirectly impact an instrument to insert or remove the implant from tissue or to perform other impacting/hammering applications. When a procedure does not require use of guide means, the base surface 5*a*, 5*b*, 5*c*, 5*d* may be used as impacting surfaces. In other procedures where a guide means may be used, the head 2*a*, 2*b*, 2*c* may be rotated approximate 90° about the axis of the shaft 3*a*, 3*b*, 3*c* (e.g., axis 12) so that the head 2*a*, 2*b*, 2*c* may be positioned on a guide means and the lateral surface 4*a*, 4*b*, 4*c* may be used as the impacting surface.

The guide rod 17 may be positioned into the recess 6*a*, 6*b*, 6*c* through the insertion channel 7*a*, 7*b*, 7*c* by tilting the impacting device 1*a*, 1*b*, 1*c*. Thereafter, the guide rod 17 may be moved in the axial channel 8*a*, 8*b*, 8*c* parallel and/or along the longitudinal axis of the head 2*a*, 2*b*, 2*c* (e.g., along the longitudinal axis 11) until the guide rod 17 is positioned in the locking chamber 9*a*, 9*b*, 9*c*. Once the head 2*a*, 2*b*, 2*c* is in the locking chamber 9*a*, 9*b*, 9*c*, the head 2*a*, 2*b*, 2*c* may be capable of rotating around the rod 17 (e.g., about axis 11). The head 2*a*, 2*b*, 2*c* may be rotated an angle θ (FIG. 4D), for example, between about +60° and about −60° and, more preferably, between about +40° and about −40°. Alternatively, locking chamber 9*a*, 9*b*, 9*c* may be formed asymmetrically such that the rod 17 may rotate an angle, for example, between about +40° and about −50°. Such asymmetry may be improve the locking of the guide rod 17 in the locking chamber 9*a*, 9*b*, 9*c*.

In an embodiment where the insertion channel 7*a*, 7*b*, 7*c* and locking chamber 9*a*, 9*b*, 9*c* may be substantially parallel to each other, the insertion channel 7*a*, 7*b*, 7*c* and locking chamber 9*a*, 9*b*, 9*c* may be spaced apart by a distance S (FIG. 4A), preferably about 10 mm apart. The distance between the insertion channel 7*a*, 7*b*, 7*c* and locking chamber 9*a*, 9*b*, 9*c* may be determined by the material used to form the head 2*a*, 2*b*, 2*c*. The distance may be chosen so that, depending on the material use, there may be sufficient dimension between the insertion channel 7*a*, 7*b*, 7*c* and locking chamber 9*a*, 9*b*, 9*c*. In this way, the head 2*a*, 2*b*, 2*c* may be sufficiently stable and/or strong. Such a construction may minimize bending of the head 2*a*, 2*b*, 2*c* during impact and/or reduce the likelihood of the head 2*a*, 2*b*, 2*c* breaking after repeated use.

The attachment of the shaft 3*a*, 3*b*, 3*c* (e.g., attachment 13 of shaft 3*b*) and the insertion channel 7*a*, 7*b*, 7*c* may be positioned approximately the same distance from the edge of the head 2*a*, 2*b*, 2*c*. The axial channel 8*a*, 8*b*, 8*c* may connect the insertion channel 7*a*, 7*b*, 7*c* and the locking chamber 9*a*, 9*b*, 9*c*, and may have a size/dimension D (FIG. 4D), for example, of about 10.5 mm. Moreover, the edges of the insertion channel 7*a*, 7*b*, 7*c*, axial channel 8*a*, 8*b*, 8*c* and/or the locking chamber 9*a*, 9*b*, 9*c* may be rounded such that, as shown in FIG. 4A, the edges E may have a radius "r" of curvature of about 5 mm.

FIGS. 7A-8C illustrate an alternative impacting device 1*d*. The impacting device 1*d* may have a head 2*d*, a shaft 3*d*, a handle 10*d* operably associated with the shaft 3*d* and a longitudinal axis 11*d*. The handle 10*d* may have one or more flattened sides. A recess 6*d* may be positioned through the lateral surface 4*d* and may not extend into/through the base surfaces 5*d*. Similar to previous impacting device 1*a*, 1*b*, 1*c*, one or both base surfaces 5*a*, 5*b*, 5*c*, 5*d* of the impacting device 1d may be uninterrupted, solid, intact or cohesive (i.e., the base surfaces 5a, 5b, 5c, 5d may not have slots or other interruptions therein).

Figure 8A:
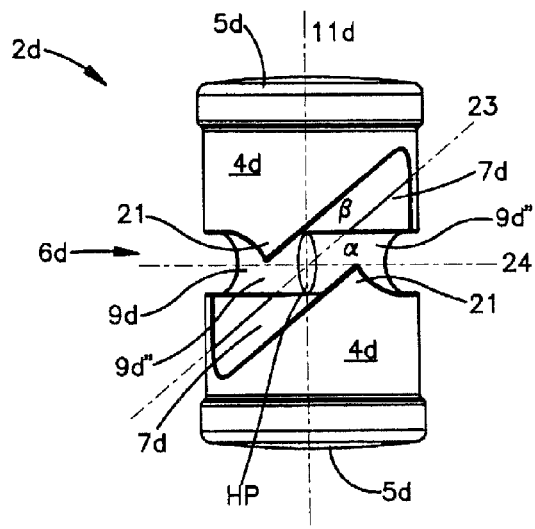
FIGS. 8A, 8B and 8C are different views of the head of the impacting device of FIGS. 7A and 7B.
Figure 8B:
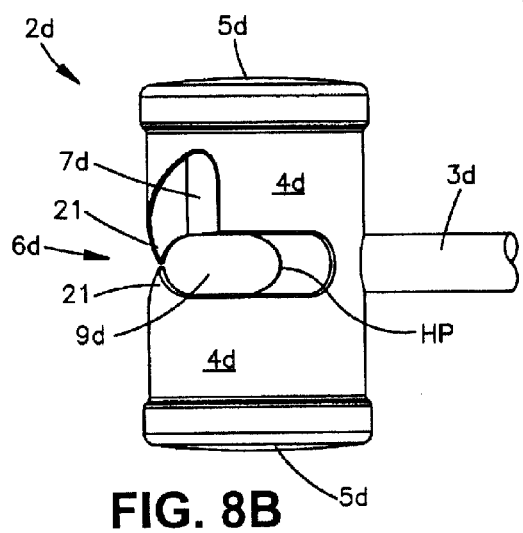
Figure 8C:
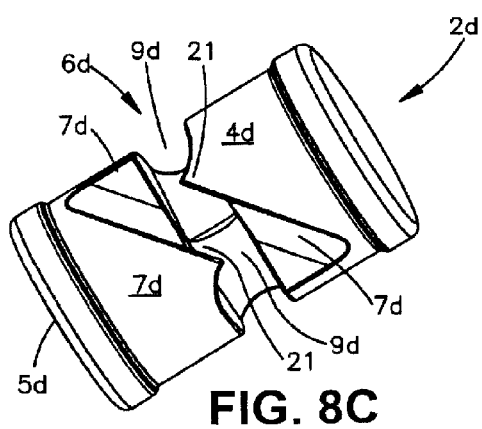

The impacting device 1d may have a recess 6d, which may have an insertion channel 7d and a locking chamber 9d. The locking chamber 9d may be horizontal and/or approximately perpendicular to the longitudinal axis 11d of the head 2d. The locking chamber 9d may be an elongated passageway or slot. The guide rod 17d may be positioned in and move within this passageway or slot 9d. As shown in FIG. 8A, the insertion channel 7d may be at an angle α with respect to the locking chamber 9d. Specifically, the angle α between the longitudinal axis 23 of the insertion channel 7d and the longitudinal axis 24 of the locking chamber 9d may be between about 20° and about 70° and, more preferably, between about 30° and about 50°. As shown in FIGS. 7A-8C, the angle α may be about 50°. The insertion channel 7d may be arranged obliquely on the head 2d relative to the longitudinal axis 11d and may be formed to permit the insertion of the guide rod 17d therethrough. There may be an angle β between longitudinal axis 11d of the head 2d and the longitudinal axis 23 of the insertion channel 7d which may be between about 20° and about 70° and, more preferably, between about 40° and about 50°. In one embodiment, the angle β may be about 40°.

Figure 9A:
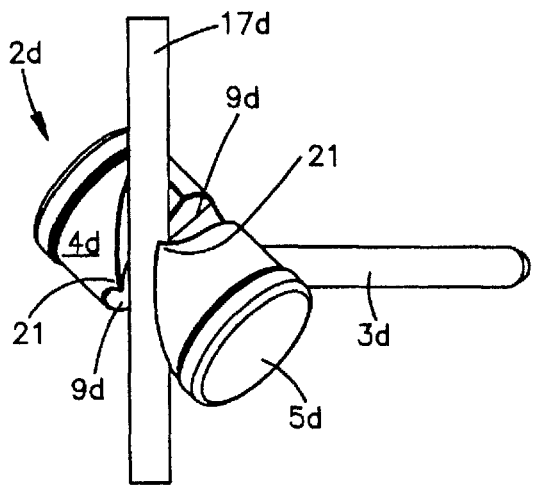
FIG. 9A-9G are different views of the impacting device of FIGS. 7A and 7B in use.
Figure 9B:
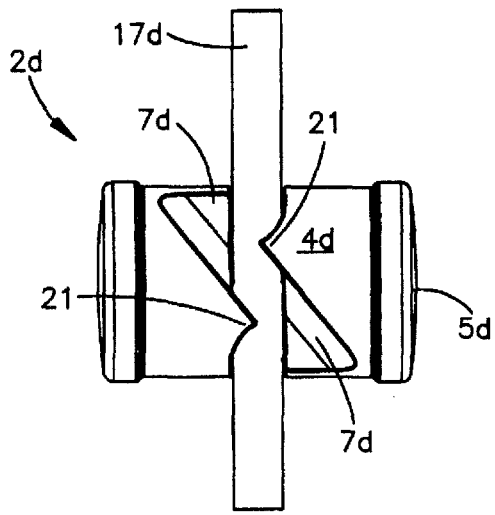
Figure 9C:
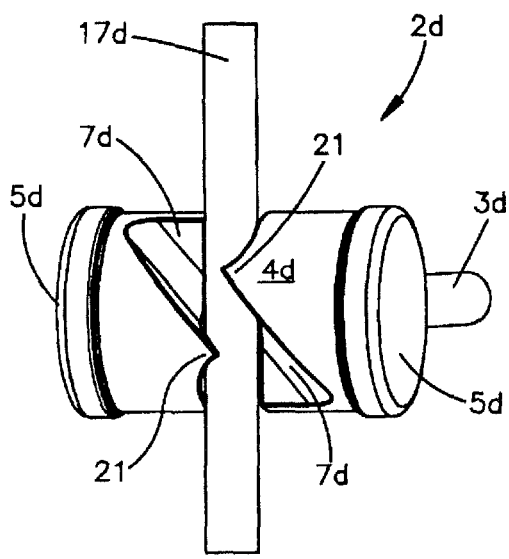
Figure 9D:
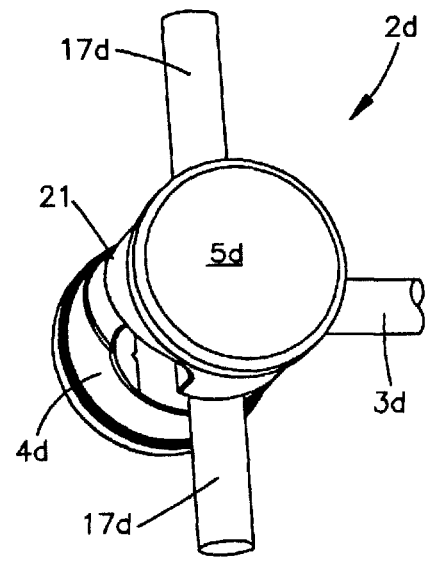
Figure 9E:
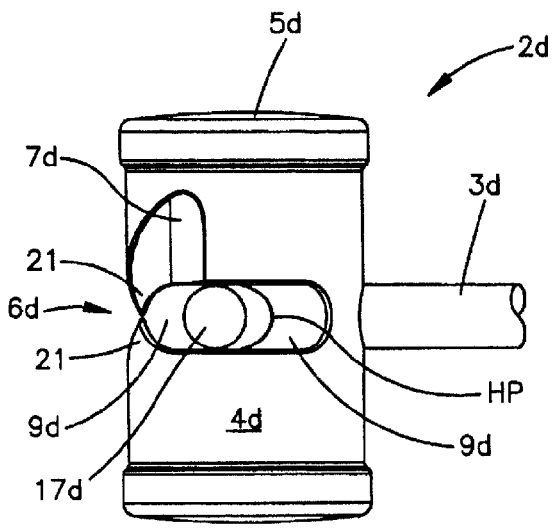

FIGS. 9A-9G illustrates the mode of operation of the head 2d. In order to insert the head 2d onto the guide rod 17d, as shown in FIG. 9A, the head 2d may be mounted obliquely on the guide rod 17d so that the guide rod 17d may be introduced into the insertion channel 7d. The head 2d may then be rotated to the position shown in FIGS. 9B and 9C. Thereafter, as shown in FIGS. 9D and 9E, the head 2d may be pushed into locking chamber 9d until the guide rod 17d comes to rest in a central position. In this state, the head 2d may be positioned onto the guide rod 17d and a surgeon may move the head 2d along the guide rod 17d (e.g., back and forth movement), for example, to insert or extract an implant.

At the lateral surface 4d, the locking chamber 9d may be bounded by at least one projection 21. In the embodiment shown in FIGS. 7A-8C, the locking chamber 9d may be bound by two projections 21. These projections 21 may be staggered relative to one another and one projection 21 may be located on each side of the insertion channel 7d. The guide rod 17d may be locked in the locking chamber 9d by the projections 21 (i.e., the projections 21 may prevent the guide rod 17d from separating from the head 2d). The projections may bound the locking chamber 9d towards the outside. Because of the design of the recess 6d and the orientation of the insertion channel 7d relative to the locking chamber 9d, the projections 21 may not be an obstacle when inserting the guide rod 17d.

Figure 9F:
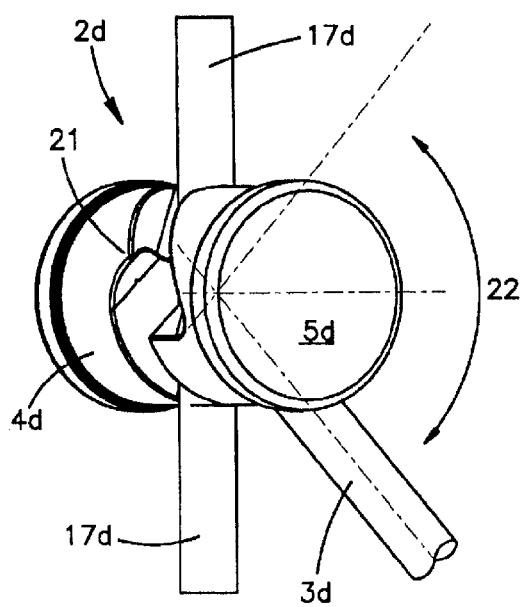
Figure 9G:
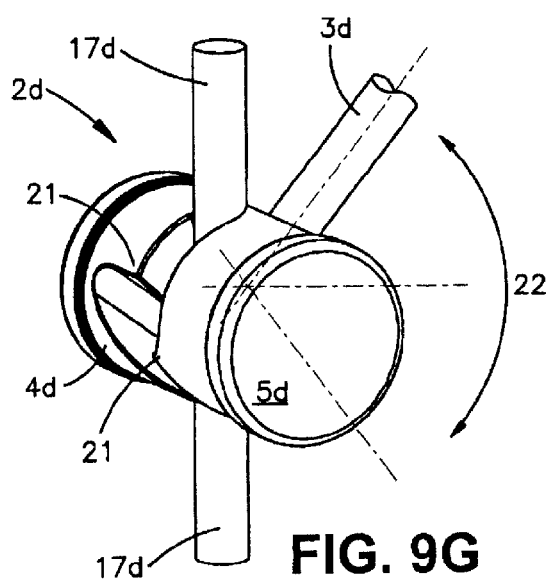

The latitude of movement, which the surgeon has when using the impacting device 1d to insert or extract implants (e.g., an intramedullary nail), is shown in FIGS. 9F and 9G. The head 2d may be moved over the guide rod 17d through an angle 22 of about 80° about the center of the head 2d. Consequently, the surgeon may move his/her hand and/or a handle of the impacting device 1d in an arc-like movement during insertion or extraction. The arc-like movement resembles natural striking movement. As shown in FIGS. 9F and 9G, the locking chamber 9d may be obliquely formed so that the guide rod 17d may be rotated about the center of the head 2d. The locking chamber 9d may be radially oriented and may have an outwardly or radially sloping surfaces 9d". For example, the radially sloping surfaces 9d" may have a highest point HP at about the center of the locking chamber 9d and may slope down in the direction of the shaft 3d such that the sloping surfaces 9d" may form a generally V-shaped surface. The rod 17d. may sit atop the highest point HP as shown in FIG. 9D and 9E. The head 2d may be rotated so that the rod 17d moves along the slopping surfaces 9d".

The head 2a, 2b, 2c, 2d may allow the surgeon considerable latitude in the actuation of the device 1a, 1b, 1c, 1d for insertion and/or extraction of an implant and may provide guidance along a guide means. The configuration of the head 2a, 2b, 2c, 2d may also prevent the head 2a, 2b, 2c, 2d from slipping off the guide means which may be used for insertion and/or extraction of an implant. Moreover, the design of the device 1a, 1b, 1c, 1d may allow the device 1a, 1b, 1c, 1d to be used similar to a conventional mallet, so that device 1a, 1b, 1c, 1d may be universally applicable.

In use, the impacting device may be used to impact an instrument such as an intramedullary rod or nail or a component attached thereto. Alternative, the impacting device may be used for other impacting/hammering applications. The impacting device may be used with a guide means which may be attached to, for example, an intramedullary rod or nail to guide movement of the impacting device. Those skilled in the art will appreciate that a guide means may be unnecessary and a surgeon may freely move the impacting device to insert/hammer an implant into tissue. The lateral surface and/or the base surfaces of the impacting device may provide an impacting surface which may be used for hammering an implant.

While the foregoing description and drawings represent the preferred embodiments of the impacting device, it will be understood that various additions, modifications and substitutions may be made therein without departing from the spirit and scope of the impacting device as defined in the accompanying claims. In particular, it will be clear to those skilled in the art that the impacting device may be embodied in other specific forms, structures, arrangements, proportions, and with other elements, materials, and components, without departing from the spirit or essential-characteristics thereof. One skilled in the art will appreciate that the system may be used with many modifications of structure, arrangement, proportions, materials, and components and otherwise, used in the practice of the system, which are particularly adapted to specific environments and operative requirements without departing from the principles of the impacting device. The presently disclosed embodiments are therefore to be considered in all respects as illustrative and not restrictive, the scope of the system being indicated by the appended claims, and not limited to the foregoing description.

What is claimed is:

1. A method for inserting or removing a device from tissue, comprising:

inserting a guide device into a first channel of a recess of a substantially cylindrical head of an impacting device in a direction perpendicular to a longitudinal axis of the head, the head having a lateral surface and at least one base surface, the recess positioned in the head and further having a second channel, the first and second channels being separated a distance from each other and connected to each other via a third channel, wherein the first and second channels intersect the lateral surface but not the base surface and the third channel extends parallel to the longitudinal axis, the first channel including a first end exposed to an exterior of the head and a second end connected to a first end of the third channel and the second channel including a first end connected to a second end of the third channel and a second end covered by the head;

moving the guide device through the third channel along the longitudinal axis;

inserting the guide device into the second channel; and rotating the guide device within the second channel so that the head is moveable along the guide device.

2. The method of claim 1, wherein the guide device is a guide rod.

3. The method of claim 1, wherein the impacting device further comprises a handle.

4. The method of claim 3, further comprising:
moving the handle in an arc relative to the guide device as the head moves along the guide device.

5. The method of claim 3, wherein the handle has at least one flat side.

6. The method of claim 1, wherein the first channel is an insertion channel for receiving the guide device via the first end of the first channel and the second channel is a locking chamber for attaching the guide device to a thread.

7. The method of claim 6, wherein the locking chamber is sized and configured so that the head is rotatable relative to the guide device about the longitudinal axis.

8. The method of claim 1, wherein the first channel is in a first plane, the second channel is in a second plane, and the third channel is in a third plane, wherein the first and second planes are parallel to one another and the third plane is perpendicular to the first and second planes.

9. The method of claim 1, wherein an angle between the first and second channels is between about 20° and 150°.

10. A method for inserting or removing a device from tissue, comprising:
inserting a guide device into a first channel of a recess of an impacting head of an impacting device, the impacting device comprising an elongated shaft extending along a first longitudinal axis, the impacting head configured to be removably attached to the shaft and extending along a second longitudinal axis angled relative to the first longitudinal axis and having a lateral surface and a base surface formed to impact a bone implant when said impacting device is attached to the shaft, the recess being positioned in the head and including a second channel connected to the first channel and angled with respect to the first channel in a first plane parallel to the second longitudinal axis and wherein the first and second channels do not intersect the base surface;
rotating the guide device to move the guide device from the first channel into the second channel; and
rotating the head about the second longitudinal axis as the head is moved along the guide device.

11. The method of claim 10, wherein the guide device is a guide rod.

12. The method of claim 10, wherein the impacting device further includes a handle coupled to the impacting head, the method further comprising: moving the handle in an arc relative to the guide device as the head moves along the guide device.

13. The method of claim 12, wherein the first channel is an insertion channel and the second channel is a locking chamber for receiving the guide device, the locking chamber having at least one projection for holding the guide device in the locking chamber, a first one of the projections being disposed at a first end of the first channel and a second one of the projections being disposed at a second end of the first channel, the first and second ones of the projections bounding the second channel towards an exterior of the head.

14. The method of claim 13, wherein the locking chamber has a first sloping surface and a second sloping surface that form a V-shape having an intersection substantially near a center of the second channel.

15. The method of claim 10, wherein the first and second channels intersect the lateral surface but not the base surface and an opposing surface opposite the base surface.

16. The method of claim 10, wherein the angle is between about 20° and about 70°.

17. The method of claim 10, wherein an angle between the second longitudinal axis and the first channel is between about 20° and 70° when viewed in the first plane.

18. The method of claim 10, wherein the head is cylindrical.

19. The method of claim 10, wherein the device further includes a handle operably associated with the shaft, wherein the handle has at least one flat side.

20. The method of claim 10, wherein both the lateral surface and the base surface intersect the second longitudinal axis.

* * * * *